United States Patent [19]

Miyazaki et al.

[11] Patent Number: 5,444,046
[45] Date of Patent: Aug. 22, 1995

[54] AMYLASE INHIBITORS

[75] Inventors: Toshiyuki Miyazaki, Fujimi; Toshihisa Morimoto, Tokyo; Ryuji Murayama, Hyogo; Hiroshi Matsubara, Osaka, all of Japan

[73] Assignees: Nisshin Flour Milling Co., Ltd., Tokyo; Nagata Sangyo Co., Ltd., Hyogo, both of Japan

[21] Appl. No.: 216,846

[22] Filed: Mar. 24, 1994

[30] Foreign Application Priority Data

Mar. 29, 1993 [JP] Japan .................................. 5-091881
May 28, 1993 [JP] Japan .................................. 5-148423

[51] Int. Cl.$^6$ .......................... A23J 1/12; A61K 38/16; C07K 1/18; C07K 14/415
[52] U.S. Cl. ..................................... 514/12; 426/656; 530/374; 530/395; 530/416
[58] Field of Search ..................... 426/656; 514/2, 12; 530/374, 375, 416, 423, 424, 425

[56] References Cited

U.S. PATENT DOCUMENTS

| | | | |
|---|---|---|---|
| 3,950,319 | 4/1976 | Schmidt et al. | 530/374 |
| 5,084,275 | 1/1992 | Maeda et al. | 530/375 |
| 5,093,315 | 3/1992 | Maeda et al. | 514/2 |
| 5,332,803 | 7/1994 | Miyazaki et al. | 530/375 |

FOREIGN PATENT DOCUMENTS

| | | |
|---|---|---|
| 0372523 | 6/1990 | European Pat. Off. . |
| 0567088A2 | 10/1993 | European Pat. Off. . |
| 3204569 | 11/1982 | Germany . |
| 61-171431 | 8/1986 | Japan . |

OTHER PUBLICATIONS

Biochimica et Biophysics Acta, vol. 828, 1985, pp. 213–221, K. Maeda, et al., "Complete Amino Acid Sequence Of An Alpha-Amylase Inhibitor In Wheat Kernel (0.19–Inhibitor)".

"The Complete Amino Acid Sequence Of A Major Wheat Protein Inhibitor Of α-Amylase", Nizar Kashlan and Michael Richardson, *Phytochemistry*, vol. 20, No. 8, pp. 1781–1784, 1981.

"New Dimeric Inhibitor Of Heterologous a-Amylases Encoded By A Duplicated Gene In The Short Arm Of Chromosome 38 Of Wheat . . . ", *Euro., J. Biochem.*, 183, pp. 37–40, 1989.

"Influence Of An a-Amylase Inhibitor (Bay d 7791) On Blood Glucose, Serum Insulin And NEFA in Starch Loading Tests in Rats, Dogs, and Man", Springer-Vorlag, *Diabetologia*, 9, pp. 99–101, 1973.

"Disc Electrophoresis-II, Method And Application To Human Serum Proteins", Baruch J. Davis, *Annals New York Academy Of Sciences*, 121, pp. 404–427, 1964.

"Studies Of Glutenin. II. Relation Of Variety, Location Of Growth, And Baking Quality To Molecular Weight Distribution Of Subunits", R. A. Orth et al., *Cereal Chemists*, vol. 50, pp. 190–197, 1973.

"Complete Amino Acid Sequence Of An α–Amylase Inhibitor In Wheat Kernel", K. Maeda, T. Hase, and H. Matsubara, *Biophysica Acta*, 743, pp. 52–57, 1983.

*Primary Examiner*—Jeffrey E. Russel
*Attorney, Agent, or Firm*—Oblon, Spivak, McClelland, Maier, & Neustadt

[57] ABSTRACT

An amylase inhibitor consisting essentially of a protein constructed of 248 amino acid residues having two subunits, each identified as SEQ ID NO:1, in which a single band is observed at a mobility of 0.26 by polyacrylamide gel electrophoresis. The amylase inhibitor can be extracted from wheat and purified by absorption on a cation exchange resin. It is useful for inhibiting an increase in blood glucose level, controlling insulin secretion, suppressing appetite, and as a food additive. The new amylase inhibitor can be used in combination with a protein composed of two subunits, each identified as SEQ ID NO:2, the total content of both proteins being not less than 20% by weight.

13 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 124 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Ser Gly Pro Trp Met Cys Tyr Pro Gly Tyr Ala Phe Lys Val Pro Ala
 1               5                  10                  15

Leu Pro Gly Cys Arg Pro Val Leu Lys Leu Gln Cys Asn Gly Ser Gln
            20                  25                  30

Val Pro Glu Ala Val Leu Arg Asp Cys Cys Gln Gln Leu Ala Asp Ile
            35                  40                  45

Ser Glu Trp Cys Arg Cys Gly Ala Leu Tyr Ser Met Leu Asp Ser Met
 50                      55                  60

Tyr Lys Glu His Gly Val Gln Glu Gly Gln Ala Gly Thr Gly Ala Phe
 65                  70                  75                  80

Pro Ser Cys Arg Arg Glu Val Val Lys Leu Thr Ala Ala Ser Ile Thr
                85                  90                      95

Ala Val Cys Lys Leu Pro Ile Val Ile Asp Ala Ser Gly Asp Gly Ala
            100                     105                 110

Tyr Val Cys Lys Gly Val Ala Ala Tyr Pro Asp Ala
            115                 120
```

( 2 ) INFORMATION FOR SEQ ID NO:2:

( i ) SEQUENCE CHARACTERISTICS:
( A ) LENGTH: 124 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Ser Gly Pro Trp Met Cys Tyr Pro Gly Gln Ala Phe Gln Val Pro Ala
 1               5                  10                  15

Leu Pro Ala Cys Arg Pro Leu Leu Arg Leu Gln Cys Asn Gly Ser Gln
            20                  25                  30

Val Pro Glu Ala Val Leu Arg Asp Cys Cys Gln Gln Leu Ala His Ile
            35                  40                  45

Ser Glu Trp Cys Arg Cys Gly Ala Leu Tyr Ser Met Leu Asp Ser Met
```

|   |   | 50 |   |   |   | 55 |   |   |   | 60 |   |   |   |   |
|---|---|---|---|---|---|---|---|---|---|---|---|---|---|---|
| Tyr | Lys | Glu | His | Gly | Ala | Gln | Glu | Gly | Gln | Ala | Gly | Thr | Gly | Ala | Phe |
| 65 |   |   |   |   | 70 |   |   |   | 75 |   |   |   |   | 80 |
| Pro | Arg | Cys | Arg | Arg | Glu | Val | Val | Lys | Leu | Thr | Ala | Ala | Ser | Ile | Thr |
|   |   |   | 85 |   |   |   |   | 90 |   |   |   |   | 95 |   |   |
| Ala | Val | Cys | Arg | Leu | Pro | Ile | Val | Val | Asp | Ala | Ser | Gly | Asp | Gly | Ala |
|   |   |   | 100 |   |   |   |   | 105 |   |   |   |   | 110 |   |   |
| Tyr | Val | Cys | Lys | Asp | Val | Ala | Ala | Tyr | Pro | Asp | Ala |
|   |   |   | 115 |   |   |   |   | 120 |

( 2 ) INFORMATION FOR SEQ ID NO:3:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Ser | Gly | Pro | Trp | Met | Cys | Tyr | Pro | Gly | Gln | Ala | Phe | Gln | Val | Pro | Ala |
|---|---|---|---|---|---|---|---|---|---|---|---|---|---|---|---|
| 1 |   |   |   | 5 |   |   |   |   | 10 |   |   |   |   | 15 |   |
| Leu | Pro | Gly | Cys | Arg | Pro | Leu | Leu | Lys | Leu | Gln | Cys | Asn | Gly | Ser | Gln |
|   |   |   | 20 |   |   |   |   | 25 |   |   |   |   | 30 |   |   |
| Val | Pro | Glu | Ala | Val | Leu | Arg | Asp | Cys | Cys | Gln | Gln | Leu | Ala | Asp | Ile |
|   |   |   | 35 |   |   |   |   | 40 |   |   |   |   | 45 |   |   |
| Ser | Glu | Trp | Pro | Arg | Cys | Gly | Ala | Leu | Tyr | Ser | Met | Leu | Asp | Ser | Met |
|   | 50 |   |   |   |   | 55 |   |   |   |   | 60 |   |   |   |   |
| Tyr | Lys | Glu | His | Gly | Val | Ser | Glu | Gly | Gln | Ala | Gly | Thr | Gly | Ala | Phe |
| 65 |   |   |   |   | 70 |   |   |   | 75 |   |   |   |   | 80 |   |
| Pro | Ser | Cys | Arg | Arg | Glu | Val | Val | Lys | Leu | Thr | Ala | Ala | Ser | Ile | Thr |
|   |   |   | 85 |   |   |   |   | 90 |   |   |   |   | 95 |   |   |
| Ala | Val | Cys | Arg | Leu | Pro | Ile | Val | Val | Asp | Ala | Ser | Gly | Asp | Gly | Ala |
|   |   |   | 100 |   |   |   |   | 105 |   |   |   |   | 110 |   |   |
| Tyr | Val | Cys | Lys | Asp | Val | Ala | Ala | Tyr | Pro | Asp | Ala |
|   |   |   | 115 |   |   |   |   | 120 |

( 2 ) INFORMATION FOR SEQ ID NO:4:

( i ) SEQUENCE CHARACTERISTICS:
        ( A ) LENGTH: 123 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ser | Gly | Pro | Trp | Ser | Trp | Cys | Asn | Pro | Ala | Thr | Gly | Tyr | Lys | Val | Ser |
|---|---|---|---|---|---|---|---|---|---|---|---|---|---|---|---|
| 1 |   |   |   | 5 |   |   |   |   | 10 |   |   |   |   | 15 |   |
| Ala | Leu | Thr | Gly | Cys | Arg | Ala | Met | Val | Lys | Leu | Gln | Cys | Val | Gly | Ser |
|   |   |   | 20 |   |   |   |   | 25 |   |   |   |   | 30 |   |   |
| Gln | Val | Pro | Glu | Ala | Val | Leu | Arg | Asp | Cys | Cys | Gln | Gln | Leu | Ala | Asp |
|   |   |   | 35 |   |   |   |   | 40 |   |   |   |   | 45 |   |   |
| Ile | Asn | Asn | Glu | Trp | Cys | Arg | Cys | Gly | Asp | Leu | Ser | Ser | Met | Leu | Arg |
|   |   |   | 50 |   |   |   |   | 55 |   |   |   |   | 60 |   |   |
| Ala | Val | Tyr | Gln | Glu | Leu | Gly | Val | Arg | Glu | Gly | Lys | Glu | Val | Leu | Pro |
| 65 |   |   |   |   | 70 |   |   |   |   | 75 |   |   |   |   | 80 |
| Gly | Cys | Arg | Lys | Glu | Val | Met | Lys | Leu | Thr | Ala | Ala | Ser | Val | Pro | Glu |
|   |   |   | 85 |   |   |   |   | 90 |   |   |   |   | 95 |   |   |
| Val | Cys | Lys | Val | Pro | Ile | Pro | Asn | Pro | Ser | Gly | Asp | Arg | Ala | Gly | Val |
|   |   |   | 100 |   |   |   |   | 105 |   |   |   |   | 110 |   |   |

```
Cys Tyr Gly Asp Trp Cys Ala Tyr Pro Asp Val
            115                 120
```

AMYLASE INHIBITORS

FIELD OF THE INVENTION

This invention relates to a new amylase inhibitor comprising specific proteins, a process for the preparation of the same from a wheat origin material and the application of such amylase inhibitor as a medicine or food.

BACKGROUND OF THE INVENTION

Intake of excessive nutrients induces secretion of a larger amount of insulin to indirectly cause a collapse of metabolic balance, thus leading to a reduction of glucose tolerating function (hyperglycemia), diabetes, hyperlipemia, arteriosclerosis, etc. Especially in diabetic patients, the insulin function is insufficient and the glucose tolerance is lowered. Consequently the blood glucose level is remarkably increased after meals, thereby causing complications such as damage to blood capillaries and arteriosclerosis. For the prevention and treatment of such diseases it is effective to ingest foods or materials which can hardly induce an increase in blood glucose level. In this respect materials capable of inhibiting or preventing hydrolysis of starch into glucose have been desired. Further, overeating contributes to diseases of adult people such as adiposity, hypertension, diabetes and cardiac diseases.

From the above aspects, various studies have been made on so-called amylase inhibitors which are effective in inhibiting the activity of amylase to hydrolyze starch. It is reported that amylase inhibitors are also contained in wheat. Since then, amylase inhibitors of wheat origin have been investigated [see, for example, U.S. Pat. No. 3,950,319, Japanese Patent Kokai 61-171431, Phytochemistry, vol. 20, No. 8, pp. 1781-1784, 1981; Eur. J. Biochem. 183, 37-40 (1989)].

However, it is reported that prior amylase inhibitors of wheat origin as mentioned above have exceedingly low or no inhibitory activity against human pancreatic α-amylase, and do not produce an effect as expected when orally given to humans, although they have some inhibitory activity against amylases of other animals than human. Therefore, there is a need for a highly active amylase inhibitor having a strong inhibitory activity against human pancreatic α-amylase and capable of effectively inhibiting an increase in blood glucose level and insulin secretion when orally administered at a low level, especially capable of effectively inhibiting hydrolysis of heated or cooked starch.

Further it is reported that an agent for inhibiting an increase in blood glucose level or insulin secretion brings about an increased level of free fatty acids in blood [Puls and Keup, "Diabetologia" 9, 97-101 (1973)]. In general, such increased levels bring about the feeling of hunger which will lead to overeating. This results in offsetting the effect of inhibiting an increase in blood glucose level and the effect of inhibiting an insulin secretion, which will make it difficult to effectively treat or prevent the diseases such as diabetes.

DETAILED DESCRIPTION OF THE INVENTION

We have found that a highly active new amylase inhibitor can be produced by treating an amylase inhibitor-containing solution extracted from a wheat origin material with water or the like, using a specific method distinguished from the prior art processes. More particularly, the specific method includes treating an extract containing the amylase inhibitor with a cation exchanger to adsorb the amylase inhibitor thereon, followed by treating the cation exchanger with an alkali solution of a specified pH to elute the amylase inhibitor and immediately making the amylase inhibitor-containing eluate acid or neutral with an acid. This method provides an eluate which contains a material having a higher amylase inhibitory activity than that of known amylase inhibitors of wheat origin, particularly a material capable of strongly inhibiting the activity of human pancreatic α-amylase. Our further study of the material of high amylase inhibitory activity recovered from the eluate with regard to molecular weight and primary structure has revealed that it is a new protein having the amino acid sequence specified below.

Thus, the invention relates to a new amylase inhibitor consisting essentially of a protein composed of two subunits, each having the following amino acid sequence:

Ser Gly Pro Trp Met Cys Tyr Pro Gly Tyr Ala Phe Lys Val Pro
1           5                   10                  15

Ala Leu Pro Gly Cys Arg Pro Val Leu Lys Leu Gln Cys Asn Gly
            20                  25                  30

Ser Gln Val Pro Glu Ala Val Leu Arg Asp Cys Cys Gln Gln Leu
            35                  40                  45

Ala Asp Ile Ser Glu Trp Cys Arg Cys Gly Ala Leu Tyr Ser Met
            50                  55                  60

Leu Asp Ser Met Tyr Lys Glu His Gly Val Gln Glu Gly Gln Ala
            65                  70                  75

Gly Thr Gly Ala Phe Pro Ser Cys Arg Arg Glu Val Val Lys Leu
            80                  85                  90

Thr Ala Ala Ser Ile Thr Ala Val Cys Lys Leu Pro Ile Val Ile Asp
            95                  100                 105

Ala Ser Gly Asp Gly Ala Tyr Val Cys Lys Gly Val Ala Ala Tyr
            110                 115                 120

Pro Asp Ala    (SEQ ID NO:1)

This sequence is identified as SEQ ID No:1 in the Sequence Listing.

The invention also relates to a process of preparing an amylase inhibitor comprising predominantly a protein composed of two subunits, each identified as SEQ ID NO:1, comprises the steps of:

(a) extracting a wheat origin material with an extracting solution to produce a solution containing the amylase inhibitor;
(b) optionally subjecting the solution to a purification treatment to remove contaminants, treating the solution with a cation exchanger to adsorb the amylase inhibitor thereon;
(c) treating the cation exchanger with an alkali solution at pH 9-13 to elute the amylase inhibitor from the cation exchanger;
(d) immediately adjusting the pH of the eluate containing the amylase inhibitor within the neutral or acidic range; and
(e) recovering from the pH adjusted solution a desired amylase inhibitor as defined above.

The new amylase inhibitor of the invention has a molecular weight of approximately 25,000 according to the gel filtration chromatography using Sephadex G-75 which will be described later. In addition, when the new amylase inhibitor of the invention was subjected to polyacrylamide gel electrophoresis according to the method of Davis described in "Annals New York Academy of Sciences", 121, pp.404–427 (1964), a single band was observed at a mobility of 0.26. By SDS-polyacrylamide electrophoresis according to the method of Orth et al described in "Cereal Chem.", vol. 50, pp. 190–197 (1973), a single band was observed at a position corresponding to a molecular weight of 12,500. These data reveal that the new amylase inhibitor of the invention is a protein composed of two subunits, each of which has a molecular weight of 12,500.

The amino acid sequence of each subunit was determined using a peptide sequencer PSQ-1 (manufactured by Shimazu Co., Ltd.), by which the subunit was found to have a structure having 124 amino acid residues identified as SEQ ID No:1. Accordingly, the amylase inhibitor of the invention is a protein constructed of 248 amino acid residues having two subunits, each identified as SEQ ID NO:1. The protein of the invention has S—S bonds.

The new amylase inhibitor of the invention is called hereafter "0.26 AI" for convenience, which has a very high inhibitory activity against an amylase, especially a human pancreatic α-amylase. The inhibitory activity of 0.26 AI is about 5–30 times higher than other amylase inhibitors of wheat origin such as 0.53 AI composed of two subunits, each identified as SEQ ID NO:3 in the Sequence Listing (Biochim. Biophys. Acta. 743, 52–57 (1983)) and 0.28 AI identified as SEQ ID NO:4 in the Sequence Listing [Phytochemistry, vol. 20, No. 8, pp. 1781–1784 (1981)].

0.26 AI of the invention includes any protein having an amylase inhibitory activity composed of two subunits, each identified as SEQ ID NO:1, regardless of the process for the preparation including those by chemical synthesis. However, 0.26 AI of the invention can be surely prepared by the process of the invention which comprises extracting a wheat origin material with water, etc., and subjecting the extract to a cation exchanger treatment, which process will be detailed below.

Process Step (a)

A wheat origin material is extracted with an extracting solution to prepare a solution containing the amylase inhibitor.

The wheat origin material includes, e.g., wheat, wheat flour and wheat gluten, any of which can be used regardless of the species, place of the production, season of the harvest, crop year, size of the particles, etc. Among them is preferably employed wheat flour (including wheat semolina) or wheat gluten because of its good extraction efficiency. 0.26 AI can be obtained in high yield from Durum wheat among various species of wheat. Therefore, Durum wheat or gluten produced therefrom are especially preferred for the wheat origin material.

The extracting solution used in step (a) includes water, an acid, an aqueous acid solution, a dilute alkali, an aqueous alcohol, a dilute salt solution, a buffer solution and the combination thereof.

For the extracting solution is preferred the aqueous acid solution at pH 2–5, water or a dilute aqueous alkali solution. An aqueous alcohol may be used. As the aqueous acid solution is preferably employed an aqueous solution adjusted to pH 2–5 with an inorganic acid such as hydrochloric or phosphoric acid or an organic acid such as acetic acid. As the dilute aqueous alkali solution is preferably employed an aqueous alkaline solution adjusted to pH 8–10 with ammonia, sodium hydroxide or the like. As the aqueous alcohol is preferably used an aqueous solution of an alcohol such as methanol, ethanol or isopropyl alcohol in an alcohol concentration of approximately 1–50%. The dilute salt solution includes e.g. the solution of a neutral salt such as sodium chloride and potassium chloride. As the buffer solution is preferably employed a phosphate buffer, an acetate buffer and a tris buffer, which are adjusted to pH 4–8.5. It is preferable that the extracting solution is maintained at a constant pH with a tris buffer or an acetate buffer.

In step (a), a process may be employed in which a sufficient amount of the extracting solution (usually about 3 to 50 times amount) is added to the wheat origin material and the extraction treatment is accomplished by stirring the mixture usually at a temperature of about 10°–40° C. followed by removal of solids by any of the means such as centrifugal separation, filtration or settlement to give an extract solution containing the amylase inhibitor. However, the process is not restricted to the above, and may optionally use as the extract solution a waste liquid or water washings of the dough or batter discharged in the recovery of starch or gluten from wheat flour. In this case the water washings of dough or batter which have been troubled in handling can effectively be utilized.

Process Step (b)

The amylase inhibitor-containing solution extracted in step (a) can be treated with a cation exchanger. Before the above treatment, said solution may be optionally subjected to any purification treatment to remove contaminants. In either case, 0.26 AI of the invention can be produced, but the purification is preferable for the preparation of 0.26 AI in a higher purity with better efficiency.

Purification before the treatment with a cation exchanger, if applied may be conducted by any purification process used in the production of amylase inhibitors from wheat. Examples of the purification processes include: Process (1) which comprises adding to the amylase inhibitor-containing extract solution obtained in step (a) an agent such as ammonium sulfate or ethanol to form precipitates containing the amylase inhibitor, collecting the precipitates and suspending them in a small amount of water, subjecting the suspension to a desalting treatment using a dialyzing membrane, adding a phosphate buffer to a desalted solution to remove the precipitate, treating the resultant supernatant with an anion exchanger such as DEAE cellulose, using a solution that has passed through the exchanger as an amylase inhibitor-containing solution either directly without further treatment or after drying to powders and dissolution of the powders in a buffer, or further hydrophobic chromatography to collect a fraction having an amylase inhibitory activity; process (2) which comprises heating the amylase inhibitor-containing extract solution obtained in step (a), for example, to 70°–90° C. to denature heat unstable protein still remaining in the solution, separating and removing the denatured products, to use the resultant solution as an amylase inhibitor-containing solution; process (3) which comprises further treating the solution obtained in process (2) by means of an ultrafiltration membrane (preferably, that having a fractionation molecular weight of 20,000 cut off) or gel filtration chromatography to remove excess salts and other low-molecular contaminants and if necessary subjecting to concentration for use as an amylase inhibitor-containing solution; and process (4) which comprises adjusting the amylase inhibitor-containing extract solution obtained in step (a) to the pH of about 3 and again adjusting the pH to neutrality to separate and remove the occurred precipitates and using the solution as an amylase inhibitor-containing solution. In particular, the above process (1) is preferred.

As the cation exchangers can be employed those such as polymeric cation exchanging resin, silicic acid and aluminum silicate. Specifically, polymeric cation exchanging resins such as CM-Toyopal (trade name, Toso Co., Ltd.) and Diaion HPK-55 (trade name, Mitsubishi Kasei Kogyo) are preferably used. The treatment with the cation exchanger may be carried out either by a batch process in which a cation exchanger is added to an amylase inhibitor-containing solution and the mixture is stirred to effect an ion exchange or by a continuous process in which an amylase inhibitor-containing solution is passed through a column filled with a cation exchanger. The continuous process is preferred. In the process it is preferred to treat the amylase inhibitor-containing solution adjusted to pH 3–5 with a cation exchanger which has been equilibrated with a buffer at pH 3–5. Then the amylase inhibitor in the solution is adsorbed on the cation exchanger.

Process Step (c)

The cation exchanger is treated with an alkali solution at pH 9–13 or with an alkali buffer at pH 9–10 to elute 0.26 AI adsorbed on the cation exchanger.

Before the above treatment, the cation exchanger may be optionally treated with a neutral solution containing sodium chloride or the like to remove by elution the impurities from the cation exchanger. The alkaline solution used in this step can include an aqueous solution of any alkali compounds such as sodium, potassium, calcium, magnesium and ammonium hydroxides with no particular restriction to the species of the alkali compound provided that the pH is 9–13. An aqueous solution of sodium hydroxide is preferred. With an aqueous solution of sodium hydroxide used, the concentration is preferably 0.05–1.0N. With an alkali buffer, the concentration is preferably 20 mM — 1M. If the pH of the alkali solution is below 9, smooth elution of the 0.26 AI amylase inhibitor from the cation exchanger cannot be achieved. If the pH of the alkali solution is above 13, 0.26 AI is denatured during elution so that a desired amylase inhibitor cannot be obtained.

Process Step (d)

An acid is immediately added to 0.26 AI-containing solution obtained in step (c), thereby adjusting the pH of the solution to 2–5 in order to prevent a modification of the amylase inhibitor contained in the alkaline eluate. The pH adjustment of the alkaline eluate with an acid may be conducted by adding an acid to the alkaline eluate reserved once in a reservoir such as a vessel, or by continuously adding an acid to a vessel while introducing the alkaline eluate into the vessel, or by introducing the alkaline solution into a vessel containing an acid solution. In any case it is required that the pH of the 0.26 AI-containing alkaline solution should be adjusted to 2–5 with an acid as soon as possible. The acid used for the pH adjustment includes an inorganic acid such as hydrochloric, sulfuric or phosphoric acid, and an organic acid such as acetic acid. Hydrochloric acid is preferable.

Process Step (e)

The 0.26 AI-containing pH adjusted solution obtained in step (d) is dried by any means such as lyophilization, drying under reduced pressure, spray drying and ball drying to obtain the desired 0.26 AI. Before the above treatment, the pH adjusted solution may be optionally subjected to dialysis or other purification treatment. The 0.26 AI possesses very high inhibitory activity against human pancreatic α-amylase and can effectively inhibit digestion of heated or cooked starch such as cooked rice, that is, hydrolysis of heated or cooked starch even when used in a small amount.

In general, physiologically functional proteins such as enzymes are susceptible to denature under a strong alkaline condition at a pH above 9. Therefore, an alkaline solution at pH 9 or higher has not been used in prior art for the preparation of the amylase inhibitors from the wheat origin material. On the contrary, the present invention enables one to use in the treatment of the cation exchanger the alkaline solution at pH 9–13 which has not been employed in the art, by which there can be produced new 0.26 AI of the invention having much higher amylase inhibitory activity than the prior amylase inhibitors of wheat origin. Quite unexpectedly, such treating operation according to the present invention can produce new 0.26 AI with superior properties.

The present invention further includes an amylase inhibitor consisting essentially of a material comprising a protein composed of two subunits, each identified as SEQ ID NO:1 (0.26 AI) in combination with a protein composed of two subunits, each identified as SEQ ID NO:2 (0.19 AI), the total content of both proteins in the material being not less than 20% by weight.

If the total content of 0.26 AI and 0.19 AI in the material is less than 20%, the amylase inhibitor provides low amylase inhibitory activity even when administered in a high level, which results in reducing the activities of inhibiting an increase in blood glucose level and controlling an insulin secretion, thus making impossible an effective use as an appetite controlling agent.

There is no upper limit too the total content of 0.26 AI and 0.19 AI in the material. Higher content of both proteins in the material provides higher amylase inhibitory activity and higher activities of inhibiting an increase in blood glucose level, controlling an insulin secretion and inhibiting an appetite. However, the upper limit for the total content of 0.26 AI and 0.19 AI in the material is preferably about 80% by weight, from the viewpoint of productivity and economy.

The material used in the invention may contain, in addition to 0.26 AI and 0.19 AI, less than 80% by weight proteins of wheat origin, peptides and other materials (e.g., starch, edible fibers, vitamins, minerals, etc). In general, it is preferable that the material including 0.26 AI and 0.19 AI constitutes not less than 70% by weight of the total weight of the wheat protein used in the invention.

0.19 AI used in combination with 0.26 AI of the invention is known and commercially available. 0.19 AI can be prepared by any method, for example, the process disclosed in European Patent Publication No. 0 567 088 A2.

The new amylase inhibitor of the invention (0.26 AI) and the wheat protein comprising 0.26 AI and 0.19 AI can be used alone or in combination with conventional carriers or adjuvants for pharmaceutical preparation in the form of a liquid preparation or a solid preparation such as granules and tablets as an agent for inhibiting an increase in blood glucose level or an agent for controlling an insulin secretion and/or an agent for inhibiting an appetite. In addition, they may be used as food additives, particularly for carbohydrate foods rich in starch such as bread and cookie or as additives for tea, soup, seasoned fish meal and spread such as butter and jam.

Thus, the present invention relates to an agent for inhibiting an increase in blood glucose level or for controlling an insulin secretion or for suppressing an appetite, which comprises, as an active ingredient, an amylase inhibitor consisting essentially of a protein composed of two subunits, each identified as SEQ ID NO:1 or a material comprising a protein composed of two subunits, each identified as SEQ ID NO:1, in combination with a protein composed of two subunits, each identified as SEQ ID No:2, the total content of both proteins in the material being not less than 20% by weight.

Further, the present invention relates to a food additive, which comprises a protein composed of two subunits, each identified as SEQ ID NO:1 or a material comprising a protein composed of two subunits, each identified as SEQ ID NO:1 in combination with a protein composed of two subunits, each identified as SEQ ID NO:2.

The amount of the 0.26 AI or the material comprising 0.26 AI and 0.19 AI administered to the humans and added to foods may adequately be controlled depending upon conditions and symptoms of the subject to be administered or nature and quantity of foods to be ingested. With the agents of the present invention, an administration in a small level can achieve high amylase inhibitory activity, high activities of inhibiting an increase in blood glucose level and controlling an insulin secretion as well as duration in feeling of satiety.

The agent for inhibiting an increase in blood glucose level, for example, with the content of 0.26 AI or the total content of 0.26 AI and 0.19 AI being 30% by weight, exhibits an activity of inhibiting an increase in blood glucose level even when administered to a healthy person at a dose of 100 mg once a day. The administration at a unit dose of 500 to 2500 mg, 3 times a day can very well inhibit an increase in blood glucose level. For diabetic, the administration at a small dose (usually, about 300–1500 mg/day) can effectively inhibit an increase in blood glucose level.

The appetite controlling agent of the invention, for example, with the content of 0.26 AI or the total content of 0.26 AI and 0.19 AI being 30% by weight, exhibits an activity of inhibiting an increase in blood glucose level even when administered to a healthy person at a dose of 100 mg once a day. The administration at a unit dose of 500 to 2500 mg, 3 times a day can very well inhibit an increase in blood glucose level. For diabetic, the administration at a small dose (usually, about 300–1500 mg/day) can effectively inhibit an increase in blood glucose level.

The appetite controlling agent of the invention, for example, with the content of 0.26 AI or the total Content of 0.26 AI and 0.19 AI being 30% by weight, can inhibit appetite by suppressing the feeling of hunger with no increase in the content of free fatty acid in blood, when given with a meal at a dose of 1000 to 5000 mg once.

Preferably, the agents of the present invention are formulated into the preparations (e.g., capsules, tablets, granules, powders, solutions, etc) so that 100 to 5000 mg, preferably 500 to 2500 mg of the active ingredient are contained in the agents when administered once. For example, a unit dose of 100 to 5000 mg can achieve sufficient and sure ingestion.

The invention is further illustrated by the following examples in which the amylase inhibitors were determined by the following procedure.

Determination of Molecular Weight by Gel Filtration Chromatography Using Sephadex G-75

A sample solution was prepared by adding 4 ml of a buffer (20 mM tris HCl, 200 mM NaCl, pH 8.0) to the amylase inhibitor. The solution was subjected to gel filtration chromatography at a flow rate of 0.5 ml/hr on a Sephadex G-75 gel filtration column (1.6 cm×90 cm) which had been equilibrated with the same buffer to determine the molecular weight.

Determination of Amino Acid Sequence

The amylase inhibitor was pyridylethylated and then hydrolyzed with V8 protease and lysyl endopeptidase (manufactured by Wako Jun-yaku). The hydrolyzed sample was subjected to HPLC to separate a hydrolyzed peptide fragment. The separated peptide fragments were analyzed using a peptide sequencer PSQ-1 (manufactured by Shimazu) for the structure starting from the peptide N terminus to determine the entire primary structure. The C terminus was determined by analysis of the amino acid liberated by hydrolysis with carboxypeptidase.

Determination of Inhibitory Activity Against Human Pancreatic α-amylase

An aqueous sample solution and human pancreatic α-amylase were added to 20 mM piperazine-N,N'-bis(2-ethanesulfonate) buffer (pH 6.9) containing 50 mM NaCl, 5 mM $CaCl_2$ and 0.02% egg white albumin. The mixture was allowed to stand at 37° C. for 30 min. and then mixed with 0.5 ml of a 1.5% soluble starch solution at pH 6.9. The resulting solution was allowed to react by maintaining at 37° C. for 10 min. followed by addition of 2.5 ml of a reaction terminator solution (0.08 M HCl and 0.4M acetic acid). To 0.2 ml of the reaction mixture was added 2.5 ml of an iodine solution (0.05% KI and 0.005% iodine), and the mixture was measured for absorbancy at 660 nm. The amylase was used in an amount sufficient to reduce the absorbancy by 80% when no sample solution was contained and the amount of the amylase inhibitor sufficient to inhibit the amylase activity by 50% was taken as 1 amylase inhibitory unit (U).

Determination of Total Protein Content

It was determined by the Kjeldahl's method using a KJELTEC AUTO 1030 analyzer (manufactured by Tecator, Sweden). A nitrogen-protein conversion factor of 5.70 was adopted.

Determination of 0.26 AI or 0.19 AI Content

A test sample was dissolved in a 0.1% aqueous solution of trifluoroacetic acid, and the solution was subjected to high performance liquid chromatography under the conditions shown below, to determine the peak area for 0.26 AI or 0.19 AI in the chromatogram. Separately, an authentic sample of 0.26 AI or 0.19 AI (purity 100%) was subjected to high performance liquid chromatography under the same condition as above to measure the peak area for 0.26 AI or 0.19 AI in the chromatogram. The 0.19 AI or 0.26 AI content in the same was calculated according to the following equation:

$$0.26\ AI\ \text{or}\ 0.19\ AI\ \text{content in the test sample (\%)} = (Sa/St) \times 100$$

wherein
  Sa=Peak area for 0.26 AI or 0.19 AI in the test sample
  St=Peak area for 0.26 AI or 0.19 AI in the authentic sample
Column
Packing material: CAPCELL PAK C18 SG120A (particle size 5 μm) (manufactured by Shiseido)
Size: 4.6 mm o×250 mm
Temperature: 50° C.
Flow rate: 1 ml/min
Detection: Absorbance at 280 nm
Mobile phase:
High pressure linear gradient elution with a time/concentration gradient shown below, consisting of
Solution A: 0.1% aqueous solution of trifluoroacetic acid; and
Solution B: aqueous solution of 80% acetonitrile and 0.1% trifluoroacetic acid Determination of Increase in Blood Glucose Level Blood glucose level was determined by the glucose oxidase method immediately after blood drawing from the forearm vein of a test subject. Increase in blood glucose level was determined by substracting the value in fasting from the value found. In the measurement by the glucose oxidase method was used Glucose-B-test Wako (manufactured by Wako Jun-yaku Kogyo).

Determination of Insulin Level

Blood was drawn from the forearm vein of a test subject and immediately centrifuged to prepare serum. Insulin level in the serum was measured by enzyme immunoassay. For the enzyme immunoassay was used Glazyme Insulin-EIA test (manufactured by Wako Jun-yaku Kogyo).

Evaluation of Duration in Feeling of Satiety

The test subjects were allowed to choose one of seven feelings shown in the ratings below:
1. Hungry and hard
2. Hungry
3. Slightly hungry
4. Feeling of neither hunger nor satiety
5. Comfortable feeling of satiety
6. Slightly heavy on the stomach
7. Heavy and hard on the stomach

EXAMPLE 1

To 500 g of Durum wheat flour was added 2 liters of water and the mixture stirred at room temperature for 3 hours. The precipitates were then removed by centrifugation, and to the supernatant was added hydrochloric acid to adjust to pH 3. The mixture was allowed to stand for 1 hour. To the supernatant was added an aqueous sodium hydroxide solution to adjust to pH 6. After allowing to stand for 1 hour, precipitates were removed by centrifugation. To the supernatant was added ammonium sulfate while stirring until saturation of 45% was achieved. After allowing to stand for 2 hours, the solution was centrifuged to recover precipitates.

To the precipitates was added 50 ml of water to prepare a suspension and the suspension was subjected overnight to desalting using a dialysis membrane (manufactured by Visking Co., Ltd.). To the desalted solution was added a phosphate buffer (pH 7.6) so as to give a concentration of 20 mM. The mixture was thoroughly stirred and then centrifuged to remove precipitates. The supernatant was passed through an anion exchange resin column ("DEAE-Toyopal Column", manufactured by Toso Co., Ltd.) which had been equilibrated with a 20 mM phosphate buffer solution. The column was thoroughly washed with the same buffer solution and fractions that had passed through the column were collected. The collected fractions were dialyzed against water and then against a 20 mM tris buffer solution containing 200 mM NaCl. After completion of the dialysis, the resulting solution was concentrated to 4 ml using a minimodule (manufactured by Asahi Kasei). The concentrate was subjected to a gel filtration column ("Sephacryl S-200", manufactured by Pharmacia) which had been equilibrated with the same buffer solution to collect the fractions with an amylase inhibitory activity. The collected fractions were dialyzed against water and acetate buffer (pH 4.0) was added at a concentration of 20 mM. The mixture was subjected to a cation exchange resin column ("CM-Toyopal Column", manufactured by Toso) which had been equilibrated with the same acetate buffer.

Then, an acetate buffer solution containing 100 mM NaCl was passed through cation exchange resin column to elute impurities. A 0.1N aqueous sodium hydroxide solution was then passed through the column to elute the 0.26 AI from the column. Immediately, hydrochloric acid was added to the eluate to adjust to pH 3.0. The solution was dialyzed against water and lyophilized to give 60 mg of a white product.

The molecular weight of the product obtained above was measured by gel filtration chromatography using Sephadex G-75. It was found approximately 25,000. The product gave a single band at a position corresponding to a molecular weight of 12,500 when subjected to SDS-polyacrylamide electrophoresis mentioned above. Accordingly, it was found that the above product was constructed of two subunits having a molecular weight of 12,500. Amino acid sequence of each subunit was determined by the above-mentioned method to find that it had a structure of 124 amino acid residues identified by sequence No. 1.

The total protein content and the 0.26 AI content in the product were measured by the method as described above. It was found 95% and 91%, respectively. In addition to the protein 0.26 AI, the product contained 4% protein contaminants and 5% moisture. The product obtained in Example 1 was determined for human pancreatic α-amylase inhibitory activity by the method as described above. The result is shown in Table 1 below.

REFERENCE EXAMPLE 1

Gluten was added to the product obtained in Example 1 to prepare a protein containing 15% of 0.26 AI, which was determined for human pancreatic α-amylase inhibitory activity. The result is shown in Table 1 below.

REFERENCE EXAMPLE 2

To 800 kg of wheat flour was added 410 lit. of water and the mixture was kneaded to form a dough. The dough was washed with 7600 lit. of water to recover 410 kg of gluten and 505 kg of wheat starch. At this stage, 6200 lit. of a waste liquid were produced. The pH of the waste liquid (aqueous extract) was adjusted with hydrochloric acid to 3, and after allowing to stand for 30 min., adjusted with ammonia to 6.5, by which insoluble matters were precipitated. The precipitates were removed to recover 5200 lit. of supernatant (I).

To the supernatant (I) was added sodium alginate so as to give a concentration of 300 ppm. The mixture was adjusted to pH 4.2 and stirred for 30 min., thus forming water-insoluble matters. They were recovered by means of a De Laval centrifuge. The recovered mass was dispersed in 10 times amount of water. The dispersion was mixed with 4.7 kg of calcium chloride, thoroughly stirred, adjusted with ammonia to pH 8.5 and allowed to stand for one hour. The solid matters were separated off by means of a De Laval centrifuge to recover 600 lit. of a supernatant.

The supernatant recovered above was neutralized with hydrochloric acid, and the neutralized solution was heated at 80° C. for 30 min. Insoluble matters thus formed were separated by means of a De Laval centrifuge to recover a supernatant. The supernatant was concentrated by means of a ultrafiltration membrane [manufactured by Nitto Denko K.K.; NTU-3250CIR (20000 Dalton cut off)], while removing excess calcium salt to give a concentrate solution (II).

140 lit. of the concentrate solution (II) were adjusted with ammonia to pH 7.5 and passed through a column (900 mm in length, 200 mm in inner diameter) in which 28 lit. of a cation exchange resin (Diaion HPK-55, manufactured by Mitsubishi Kasei K.K.) has been packed, at a flow rate of 1 lit./min. Fractions not adsorbed on and eluted from the cation exchange resin were collected. The eluted fractions were filtered through a ceramic filter for elimination of microbials and then lyophilized to give 1400 g of dry powder product.

The dry powder product was determined for the total protein content and the 0.19. AI content. It was found 84% and 21%, respectively. The human pancreatic α-amylase inhibitory activity is shown in Table 1 below.

REFERENCE EXAMPLE 3

The concentrate solution (II) obtained in Reference Example 2 was dried to powders. The total protein content and 0.19 AI content in the powders were measured. It was found 60% and 15%, respectively. The human pancreatic α-amylase inhibitory activity is shown in Table 1 below.

COMPARATIVE EXAMPLES 1 & 2

For comparison, known amylase inhibitors, 0.53 AI identified by sequence No. 3 and 0.28 AI identified by Sequence No. 4 were measured for human α-amylase inhibitory activity. The result is shown in Table 1 below.

TABLE 1

|  | Total protein content (%) | Content of amylase inhibitor in protein (%) | Amylase inhibitory activity (U/mg) |
| --- | --- | --- | --- |
| Product of Example 1 | 95 | 0.26 AI 91 | 23,300 |
| Product of Reference Example 1 | 99 | 0.26 AI 15 | 1,350 |
| Product of Reference Example 2 | 84 | 0.19 AI 21 | 3,550 |
| Product of Reference Example 3 | 60 | 0.19 AI 15 | 2,160 |
| Comparative Example 1 | 100 | 0.53 AI 100 | 3,940 |
| Comparative Example 2 | 100 | 0.28 AI 100 | 840 |

Table 1 shows that 0.26 AI of the invention has a very high amylase inhibitory activity as compared with known amylase inhibitors 0.53 AI and 0.28 AI.

EXAMPLE 2

Two non-diabetic healthy males and one female were each given 250 g of cooked rice and 200 ml of sugarless tea. Blood was drawn at 30 min. intervals after meal, and an increase in blood glucose level was measured by the above-mentioned method using a kit ("Glucose-B-test Wako", manufactured by Wako Jun-yaku). One week later, a test was conducted using the same persons in the same way as above except that the cooked rice contained 350 mg of 0.26 AI of the invention. The results are shown in Table 2.

TABLE 2

|  | Increase in blood glucose level (mg/dl) | |
| --- | --- | --- |
|  | Control (0.26 AI not added) | Inventive (0.26 AI added) |
| Male 1 | | |
| After 0 min. | 0 | 0 |
| 30 min. | 74 | 55 |
| 60 min. | 90 | 52 |
| 90 min. | 54 | 29 |
| Male 2 | | |
| After 0 min. | 0 | 0 |
| 30 min. | 40 | 24 |
| 60 min. | 30 | 29 |
| 90 min. | 22 | 3 |
| Female | | |
| After 0 min. | 0 | 0 |
| 30 min. | 49 | 49 |
| 60 min. | 75 | 41 |
| 90 min. | 58 | 39 |

Table 2 shows that 0.26 AI of the invention is also effective in inhibiting digestion of heated or cooked starch and inhibits hydrolysis of the starch by inhibition of human pancreatic α-amylase, thus inhibiting increase in blood glucose level.

EXAMPLE 3

The white product obtained in Example 1 was purified by conventional means to prepare a purified 0.26 AI. The dry powder product obtained in Reference Example 2 was purified by conventional means to prepare a purified 0.19 AI amylase inhibitor. The total protein content (A), content of the amylase inhibitor in protein (B) and amylase inhibitory activity (C) of the purified product were determined with the following result.

|  | A (%) | B (%) | C (U/mg) |
| --- | --- | --- | --- |
| 0.26 AI | 100 | 100 | 26100 |
| 0.19 AI | 100 | 100 | 20300 |

The purified 0.26 AI and the purified 0.19 AI were mixed in the ratio shown in Table 3 to evaluate the amylase inhibitory activity of the mixture. The result is shown in Table 3 below.

TABLE 3

| Mixed ratio | | Amylase inhibitory activity |
| --- | --- | --- |
| 0.19 AI (%) | 0.26 AI (%) | (U/mg) |
| 5 | 20 | 6300 |
| 10 | 15 | 5600 |
| 20 | 5 | 5100 |
| 5 | 35 | 9800 |

TABLE 3-continued

| Mixed ratio | | Amylase inhibitory activity |
|---|---|---|
| 0.19 AI (%) | 0.26 AI (%) | (U/mg) |
| 20 | 20 | 8900 |
| 30 | 10 | 8400 |

EXAMPLE 4

Two non-diabetic healthy males and one female, after fasted for 10 hours, were each given 300 g of cooked rice and 200 ml of sugarless tea. Blood was drawn at 30 min. intervals after meal to determine blood glucose level and insulin level, and to evaluate the duration in feeling of satiety. The test was run five times in total at one week interval for each subject, by giving to the subject sugarless tea containing 350 mg each the product of Example 1 for the first run, the product of Reference Example 1 for the second run, the product of Example 2 (20/20 mixture of 0.26 AI/0.19 AI) for the third run and the product of Reference Example 3 for the fourth run.

In the fifth run, the subject received the cooked rice and the sugarless tea free of the product (Control). The results are shown in Table 4 below.

TABLE 4

|  | Example 1 | Reference Example 1 | Example 2 | Reference Example 3 | Control |
|---|---|---|---|---|---|
| Blood glucose level (mg/dl): | | | | | |
| Before meal | 101 | 103 | 101 | 99 | 102 |
| After meal | | | | | |
| 30 min. | 128 | 158 | 141 | 167 | 162 |
| 60 min. | 150 | 187 | 155 | 178 | 183 |
| 90 min. | 145 | 151 | 148 | 140 | 148 |
| 120 min. | 116 | 130 | 123 | 127 | 124 |
| Insulin level ($\mu$U/ml): | | | | | |
| Before meal | 9 | 12 | 8 | 10 | 8 |
| After meal | | | | | |
| 30 min. | 14 | 27 | 15 | 25 | 23 |
| 60 min. | 26 | 38 | 30 | 35 | 32 |
| 90 min. | 22 | 30 | 24 | 36 | 33 |
| 120 min. | 20 | 33 | 21 | 33 | 30 |
| Feeling of Satiety: | | | | | |
| Before meal | 1.9 | 1.7 | 2.0 | 2.1 | 2.1 |
| After meal | | | | | |
| 30 min. | 5.3 | 4.9 | 5.0 | 4.9 | 4.8 |
| 60 min. | 4.3 | 4.0 | 4.4 | 4.0 | 4.1 |
| 90 min. | 4.9 | 3.3 | 4.8 | 3.7 | 3.5 |
| 120 min. | 4.1 | 3.1 | 3.7 | 3.2 | 3.0 |

Table 4 shows that the amylase inhibitor of the present invention obtained in Examples 1 and 2 containing at least 20% of either 0.26 AI or 0.19 AI are effective for the inhibition of increase in blood glucose level and for the inhibition of insulin secretion and can bring about duration in the feeling of satiety.

EXAMPLE 5

To 6.2 tons of a waste liquid of water washings of the dough discharged in the recovery of starch and gluten from wheat flour was added hydrochloric acid to adjust to pH 3.0. The mixture was allowed to stand for 30 minutes and adjusted to pH 6.5 with ammonia to precipitate insoluble matters. The precipitate was removed to recover 5.2 tons of a supernatant. To the supernatant was added 300 ppm of sodium alginate. The mixture was adjusted with hydrochloric acid to pH 4.2, stirred for 30 minutes and centrifuged to recover precipitates (65 kg). To the precipitates were added 650 liters of water to form a dispersion, to which was added 4.7 kg of calcium chloride and well stirred. The mixture was adjusted with ammonia to pH 8.5 and allowed to stand for one hour. The precipitates were removed by centrifuge to recover 600 liters of supernatant. To the supernatant was added sodium phosphate so as to give a concentration of 0.1%, the mixture was adjusted with ammonia to pH 6.5 and heat treated at 80° C. for 15 minutes. The heat denatured precipitates were removed by centrifuge, desalted and concentrated using a ultrafiltration membrane (manufactured by Nitto Denko K.K., NTU-3250 CIR, 200 Dalton cut off) and lyophilized to give 1.4 kg of dry powders.

The dry powders (500 mg) were dissolved in a 20 mM acetate buffer solution (pH 4.0) containing 5 ml of 100 mM of NaCl. Insoluble matters were removed by centrifuge. The resulting solution was subjected to gel filtration chromatography using Sephadex G-100. The active peak was separated and dialyzed at 4° C. overnight against 20 mM acetate buffer (pH 4.0) using a dialyzing tube. The dialyzed solution was passed through CM-Toyopal which had been equilibrated with the same buffer to adsorb a target material thereon. The adsorbed material was passed through 20 mM acetate buffer (pH 4.0) containing 300 mM sodium chloride to elute impurities. Then, the target material was eluted with 0.05 N sodium hydroxide solution (pH 12.2). The eluate was immediately adjusted with HCl to pH 3.0, thoroughly desalted using a dialyzing tube and lyophilized to give white powders. The resultant white powders were determined for total protein content and 0.26 AI content, which were found 94% and 88%, respectively. The human pancreatic $\alpha$-amylase inhibitory activity was determined as 22030 U/mg.

EXAMPLE 6

To 100 g of wheat flour was added one liter of 1% NaCl solution, the mixture was stirred at room temperature for 2 hours and centrifuged to separate a supernatant. To the supernatant was added ammonium sulfate until a 50% saturation was achieved. The mixture was stirred at room temperature for one hour and left to stand for one hour.

Separation by centrifugation gave precipitates to which was added 200 ml of a distilled water to disperse it. The dispersion was dialyzed overnight against a deionized water. To the dialyzed solution was added hydrochloric acid to adjust to pH 4.0 and then the remaining precipitates were removed by centrifugation. The resultant solution was passed through a CM-Sepharose column which had been equilibrated with an acetate buffer (20 mM, pH 4.0) to adsorb a target material on a resin. The resin was thoroughly washed with the same buffer and impurities were eluted with 20 mM acetate buffer (pH 4.0) containing 400 mM NaCl. The target material was eluted with 0.05 N NaOH (pH 12.2), adjusted with HCl to pH 3.0, and thoroughly dialyzed against 50 mM acetate buffer solution (pH 4.0) containing 100 mM NaCl. The dialyzed solution was concentrated by passing through an ultrafiltration membrane (M.W. 20,000) and subjected to gel filtration chromatography (20 mM acetate buffer, pH 4.0, 100 mM sodium chloride) using Sephadex G-75 for further purification. The purified product was thoroughly dialyzed against a deionized water using a dialyzing tube and lyophilized to obtain white powders. The resultant white powders were determined for the total protein content and 0.26 AI content, which were found 96% and 93%, respectively. The human pancreatic α-amylase inhibitory activity was determined as 23500 μ/mg.

What is claimed is:

1. A purified protein composed of two subunits, each having the following amino acid sequence:

```
Ser Gly Pro Trp Met Cys Tyr Pro Gly Tyr Ala Phe Lys Val Pro
 1               5              10                    15
Ala Leu Pro Gly Cys Arg Pro Val Leu Lys Leu Gln Cys Asn Gly
           20              25              30
Ser Gln Val Pro Glu Ala Val Leu Arg Asp Cys Cys Gln Gln Leu
               35              40              45
Ala Asp Ile Ser Glu Trp Cys Arg Cys Gly Ala Leu Tyr Ser Met
           50              55              60
Leu Asp Ser Met Tyr Lys Glu His Gly Val Gln Glu Gly Gln Ala
               65              70              75
Gly Thr Gly Ala Phe Pro Ser Cys Arg Arg Glu Val Val Lys Leu
           80              85              90
Thr Ala Ala Ser Ile Thr Ala Val Cys Lys Leu Pro Ile Val Ile Asp
           95              100             105
Ala Ser Gly Asp Gly Ala Tyr Val Cys Lys Gly Val Ala Ala Tyr
           110             115             120
           Pro Asp Ala   (SEQ ID NO:1)
``` having at least 23,300 μmg of human pancreatic α-amylase inhibitory activity.

2. A process of preparing an amylase inhibitor comprising predominantly a protein composed of two subunits, each identified as SEQ ID NO:1, comprising the steps of:
   (a) extracting a wheat origin material with an extracting solution to produce a solution containing the amylase inhibitor;
   (b) treating the solution with a cation exchanger to adsorb the amylase inhibitor thereon;
   (c) treating the cation exchanger with an alkali solution at pH 9-13 to elute the amylase inhibitor from the cation exchanger;
   (d) immediately adjusting the pH of the eluate containing the amylase inhibitor to within the neutral or acidic range; and
   (e) recovering from the pH adjusted eluate the amylase inhibitor as defined above.

3. A process of claim 2 wherein the wheat origin material is selected from the group consisting of wheat, wheat flour and wheat gluten.

4. A process of claim 2 wherein the extracting solution is selected from the group consisting of water, an acid, an aqueous acid solution, a dilute alkali, an aqueous alcohol, a dilute salt solution and a buffer solution.

5. A process of claim 2 wherein the solution obtained in step (a) is a water liquid or water washings of the dough or batter discharged in the recovery of starch or gluten from wheat flour.

6. An amylase inhibitor comprising a protein composed of two subunits, each identified as SEQ ID NO:1, in combination with a protein composed of two subunits, each identified as SEQ ID NO:2, the total content of both proteins in the amylase inhibitor being not less than 20% by weight.

7. An agent for inhibiting an increase in blood glucose level which comprises as an active ingredient at least 30 wt. % of a protein composed of two subunits, each identified as SEQ ID NO:1.

8. An agent for controlling insulin secretion which comprises as an active ingredient at least 30 wt. % of a protein composed of two subunits, each identified as SEQ ID NO:1.

9. An agent for inhibiting an increase in blood glucose level which comprises as an active ingredient a protein composed of two subunits, each identified as SEQ ID NO:1, in combination with a protein composed of two subunits, each indentified as SEQ ID NO:2, the total content of both proteins in the active ingredient being not less than 20% by weight.

10. An agent for controlling insulin secretion which comprises as an active ingredient a protein composed of two subunits, each identified as SEQ ID NO:1, in combination with a protein composed of two subunits, each identified as SEQ ID NO:2, the total content of both proteins in the active ingredient being not less than 20% by weight.

11. An agent for suppressing an appetite which comprises as an active ingredient at least 30 wt. % of a protein composed of two subunits, each identified as SEQ ID NO:1.

12. An agent for suppressing an appetite which comprises as an active ingredient a protein composed of two subunits, each identified as SEQ ID NO:1, in combination with a protein composed of two subunits, each identified as SEQ ID NO:2, the total content of both proteins in the active ingredient being not less than 20% by weight.

13. A food additive, which comprises at least 20 wt. % of a protein composed of two subunits, each identified as SEQ ID NO:1 or which comprises a first protein composed of two subunits, each identified as SEQ ID NO:1, in combination with a second protein composed of two subunits, each identified as SEQ ID NO:2 wherein the weight ratio of said first and second proteins is from 7:1 to 1:1, and the total content of both proteins being not less than 20 wt. %.

* * * * *

UNITED STATES PATENT AND TRADEMARK OFFICE
CERTIFICATE OF CORRECTION

PATENT NO. : 5,444,046
DATED : August 22, 1995
INVENTOR(S) : Toshiyuki MIYAZAKI, et al.

It is certified that error appears in the above-indentified patent and that said Letters Patent is hereby corrected as shown below:

Column 19, line 34 please delete "23,300 µmg" and insert therefore --23,300 U/mg--

Signed and Sealed this

Fifth Day of March, 1996

Attest:

BRUCE LEHMAN

Attesting Officer

Commissioner of Patents and Trademarks